United States Patent
Huang

(10) Patent No.: US 9,864,219 B2
(45) Date of Patent: Jan. 9, 2018

(54) DEVICE FOR DETECTING LIQUID CRYSTAL MODULE AND METHOD FOR DETECTING QUANTITY OF LIQUID CRYSTAL

(71) Applicant: SHENZHEN CHINA STAR OPTOELECTRONICS TECHNOLOGY CO., LTD., Shenzhen, Guangdong (CN)

(72) Inventor: Xiaoyu Huang, Shenzhen (CN)

(73) Assignee: Shenzhen China Star Optoelectronics Technology Co., Ltd., Shenzhen, Guangdong (CN)

( * ) Notice: Subject to any disclaimer, the term of this patent is extended or adjusted under 35 U.S.C. 154(b) by 87 days.

(21) Appl. No.: 14/240,357

(22) PCT Filed: Jan. 28, 2014

(86) PCT No.: PCT/CN2014/071660
§ 371 (c)(1),
(2) Date: Feb. 21, 2014

(87) PCT Pub. No.: WO2015/003490
PCT Pub. Date: Jan. 15, 2015

(65) Prior Publication Data
US 2015/0153592 A1 Jun. 4, 2015

(30) Foreign Application Priority Data
Jul. 11, 2013 (CN) .......................... 2013 1 0292119

(51) Int. Cl.
*G01N 3/00* (2006.01)
*G02F 1/13* (2006.01)
(Continued)

(52) U.S. Cl.
CPC .......... *G02F 1/1309* (2013.01); *G02F 1/1303* (2013.01); *G02F 1/133308* (2013.01);
(Continued)

(58) Field of Classification Search
CPC ....... G01L 5/00; G01L 5/0028; G01L 5/0038; G01N 2203/0085; G01N 2203/0019; G01N 2203/0033; G01N 3/30
(Continued)

(56) References Cited

U.S. PATENT DOCUMENTS
4,542,639 A * 9/1985 Cawley ..................... G01N 3/30
 73/12.09
7,243,530 B2 * 7/2007 Takeda ................... G01P 15/135
 73/65.01
(Continued)

FOREIGN PATENT DOCUMENTS
CN 101067689 A 11/2007
CN 101158757 A 4/2008
(Continued)

OTHER PUBLICATIONS
International Search Report dated Apr. 24, 2014, issued to the corresponding International Application No. PCT/CN2014/071660.

*Primary Examiner* — Jonathan Dunlap
(74) *Attorney, Agent, or Firm* — Kim Winston LLP

(57) ABSTRACT

The present disclosure relates to a device for detecting a liquid crystal module and a method for detecting the quantity of liquid crystal. The method includes a cover for fixedly accommodating the liquid crystal module. An accommodation space for accommodating collision units is formed between the liquid crystal module and the cover, the collision units being connected to the top wall of the cover through elastic members. The collision units are spaced from the liquid crystal module in a certain distance in a static status, and collide with a panel of the liquid crystal module through vibration of the cover in the vertical direction during detection. The device for detecting a liquid crystal module improves the detection efficiency.

8 Claims, 1 Drawing Sheet

(51) Int. Cl.
*G02F 1/1333* (2006.01)
*G01L 5/00* (2006.01)
*G01N 3/30* (2006.01)

(52) U.S. Cl.
CPC .......... *G01L 5/0028* (2013.01); *G01L 5/0038* (2013.01); *G01N 3/30* (2013.01); *G01N 2203/0019* (2013.01); *G01N 2203/0033* (2013.01); *G01N 2203/0085* (2013.01)

(58) Field of Classification Search
USPC .................. 73/12.01–12.14, 11.01–11.08
See application file for complete search history.

(56) References Cited

U.S. PATENT DOCUMENTS

| | | | | |
|---|---|---|---|---|
| 7,370,538 | B2* | 5/2008 | Suda | G01N 3/08 73/12.05 |
| 7,516,646 | B2* | 4/2009 | Makimoto | G01M 7/08 73/12.12 |
| 7,856,340 | B2* | 12/2010 | Kaneko | G01D 1/18 271/258.01 |
| 8,590,394 | B2* | 11/2013 | Liao | G01N 3/22 73/794 |
| 8,881,598 | B2* | 11/2014 | Duan | G02F 1/1309 73/818 |
| 2005/0223784 | A1* | 10/2005 | Takeda | G01P 15/135 73/65.01 |
| 2014/0109683 | A1* | 4/2014 | Duan | G01L 5/00 73/818 |
| 2014/0260526 | A1* | 9/2014 | Tsutsui | G01L 5/0028 73/12.01 |

FOREIGN PATENT DOCUMENTS

| | | |
|---|---|---|
| CN | 103091881 A | 5/2013 |
| CN | 103345081 A | 10/2013 |
| JP | 2000-258743 A | 9/2000 |
| JP | 2001-272641 A | 10/2001 |

* cited by examiner

DEVICE FOR DETECTING LIQUID CRYSTAL MODULE AND METHOD FOR DETECTING QUANTITY OF LIQUID CRYSTAL

FIELD OF THE INVENTION

The present disclosure relates to the field of detection of liquid crystal modules, in particular to a device for detecting a liquid crystal module. The present disclosure also relates to a method for detecting the quantity of liquid crystal by using the device.

BACKGROUND OF THE INVENTION

A thin film transistor liquid crystal display (TFT-LCD) controls penetration of light by using optical anisotropy and birefringent characteristic of liquid crystal molecules through a TFT switch and input of signal voltage so as to display images. In a liquid crystal display panel, a color filter substrate and a TFT substrate are boxed together through sealant, and a photo spacer is supported between the two substrates to form a certain cell gap, so that a liquid crystal filling space for filling liquid crystal is formed between the two substrates. The arrangement direction of the liquid crystal molecules in the liquid crystal filling space will be changed under the influence of an external electric field, so as to control the quantity of light passing through the color filter substrate. A liquid crystal module indicates a finished product formed after a back light unit is assembled on the liquid crystal display panel.

When the liquid crystal filling quantity in the liquid crystal display panel is insufficient, or in the presence of air generated during filling and other reasons, after the liquid crystal display panel is boxed, liquid crystal bubbles possibly appear and thus cause abnormity of a product. The present detecting methods include: (1) flapping the surface of the liquid crystal display panel by hands to determine whether liquid crystal bubbles appear in the product; (2) pressing each position of the surface of the liquid crystal display panel by using a pressing bar to determine whether liquid crystal bubbles appear in the product; and (3) dropping a steel ball along a cylindrical steel tube from a certain fixed height to collide with the surface of the liquid crystal display panel, so as to determine whether liquid crystal bubbles appear in the product. All of these detecting methods are single-point static determining methods, and it is difficult to indicate the overall condition of the liquid crystal display panel. If the overall condition of the liquid crystal display panel needs to be indicated, then multiple times of detection are needed at multiple positions of the liquid crystal display panel. The operation thereof is obviously tedious.

SUMMARY OF THE INVENTION

Starting from the above-mentioned technical problems in the prior art, the present disclosure proposes a device for detecting a liquid crystal module to improve the accuracy of abnormity detection of liquid crystal quantity in the liquid crystal module.

The present disclosure also relates to a method for detecting the quantity of liquid crystal by using the device.

According to a first aspect of the present disclosure, a device for detecting a liquid crystal module is provided, including a cover for fixedly accommodating the liquid crystal module, wherein an accommodation space for accommodating collision units is formed between the liquid crystal module and the cover, the collision units being connected to the top wall of the cover through elastic members, and wherein the collision units are spaced from the liquid crystal module in a certain distance in a static status, and collide with a panel of the liquid crystal module through vibration of the cover in the vertical direction during detection.

Through the device of the present disclosure, the collision units are connected to the top wall of the cover through the elastic members, so that the collision units can merely collide with predetermined positions of the panel. In this case, the positions where the panel has statistically maximum abnormity probability can be detected, thus achieving a high pertinency. Also, the detection efficiency is improved, and blind detection with low efficiency is avoided. The elastic members can also store a part of energy, so that collision can be completed without greatly vibrating the cover, thus prolonging the service life of the detection device. In addition, multiple collision units collide with the panel of a liquid crystal module to be detected in a dynamic and multi-point mode, so that whether liquid crystal bubbles appear in the product after collision can be determined in a better and more accurate way, and whether the quantity of liquid crystal added is abnormal can be determined more accurately.

In an embodiment, the elastic members are connected to the top wall of the cover in a movable mode. In this case, a detector can detect not only the predetermined positions of the panel, but also other positions as required. Thus the device can be conveniently used.

In an embodiment, the elastic members are springs. The springs are selected to ensure that the collision units can effectively collide with the panel of the liquid crystal module but do not damage the panel.

In an embodiment, the surfaces of the collision units, which can contact the panel of the liquid crystal module, are spherical surfaces. In this case, during collision, the collision units do not damage, for example, scratch the panel. Preferably, the collision units are balls.

In an embodiment, when the device is in the static status, the distance between the lower surface of each collision unit and the panel of the liquid crystal module is 2 to 3 times the height of the collision unit. Thus, the collision units can move with a large enough amplitude, so as to implement sufficient collision to the panel of the liquid crystal module.

In an embodiment, the cover includes side walls extending downwards from the top wall, and a connector for fixing the liquid crystal module is arranged on each side wall. Through this structure, the liquid crystal module can be conveniently fixed in the cover, so as to bring convenience to the operation of a user.

In an embodiment, the device further includes a vibrating platform for applying vertical vibration, and the lower end of each side wall is connected with the vibrating platform through a fixing member. The vibrating platform can apply vibration with constant amplitude, so as to ensure the accuracy of detection. With the vibrating platform, the detector can easily use the device.

According to a second aspect of the present disclosure, a method for detecting the quantity of liquid crystal with the above-mentioned device for detecting the liquid crystal module is proposed, including the following steps:

(a) providing a cover, and arranging a plurality of collision units connected with the top wall of the cover through elastic members respectively in the cover;

(b) fixedly accommodating a liquid crystal module to be detected in the cover in such a manner that the liquid crystal module is spaced from the collision units in a certain distance, a panel of the liquid crystal module facing the collision units;

(c) vertically vibrating the cover so that the collision units collide with the panel of the liquid crystal module; and (d) stopping vibration of the cover, and taking the liquid crystal module out for analyzing.

In an embodiment, after step (d), the elastic members are moved, and then the cover is vertically vibrated again to collide with other positions of the panel of the liquid crystal module. In this case, the detector can perform a relatively comprehensive detection as required.

In the context, the term "below" indicates the direction pointed by gravity, the term "vertical direction" indicates the direction along the gravity, and the term "horizontal direction" indicates the direction vertical to the vertical direction.

Compared with the prior art, the present disclosure has the following advantages. The collision units are connected to the top wall of the cover through the elastic members, so that the collision units can merely collide with predetermined positions of the panel. In this case, the positions where the panel has statistically maximum abnormity probability can be detected, thus achieving a high pertinency and improving the detection efficiency. In addition, the elastic members can be moved in the top wall of the cover to move the collision units, so that the detector can detect not only the predetermined positions of the panel, but also other positions of the panel as required. Thus the device can be conveniently used. Moreover, multiple collision units collide with a panel of a liquid crystal module to be detected in a dynamic and multi-point mode, so that whether liquid crystal bubbles appear in a product after collision can be determined in a better and more accurate way, and whether the quantity of liquid crystal added is abnormal can be determined more accurately.

BRIEF DESCRIPTION OF THE DRAWINGS

The present disclosure will be described in more detail below based on a certain embodiments with reference to the accompanying drawings, in which.

In the accompanying drawings, the same components are indicated by the same reference signs. The accompanying drawings are not drawn in an actual scale.

DETAILED DESCRIPTION OF THE EMBODIMENTS

The present disclosure will be further illustrated below in conjunction with the accompanying drawings.

Figure 1:
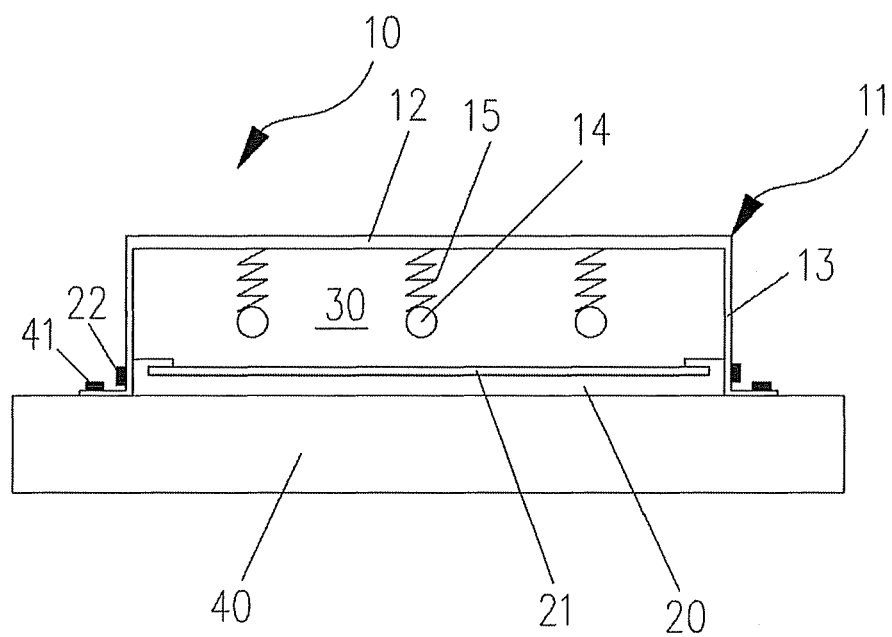
FIG. 1 is a structural schematic diagram of a device for detecting a liquid crystal module according to the present disclosure.

FIG. 1 schematically shows a device 10 for detecting a liquid crystal module according to the present disclosure (referred to as device 10 below). The device 10 includes a cover 11 and a plurality of collision units 14 connected to the top wall 12 of the cover 11 through elastic members 15 respectively.

Before collision detection, the liquid crystal module 20 needs to be fixedly mounted in the cover 11. As shown in FIG. 1, when the mounting is completed, an accommodation space 30 is formed between the top wall 12 and the liquid crystal module 20. The collision units 14 are located in the accommodation space 30 and spaced from a panel 21 of the liquid crystal module 20 with a certain distance, so that the collision units 14 can move with large, enough amplitude. In this manner, sufficient impact can be applied to the panel 21 of the liquid crystal module. In an embodiment, the distance between each collision unit 14 and the panel 21 of the liquid crystal module 20 is 2 to 3 times the height of the collision unit 14.

To facilitate mounting of the liquid crystal module 20, in an embodiment, the cover 11 further includes side walls 13 extending downwards from the top wall 12, and a connector 22 for fixing the liquid crystal module 20 is arranged on the inner surface of each side wall 13. In addition, the cross section of the cover 11 including the top wall 12 and the side walls 13 can be formed as having the same shape as the liquid crystal module 20, e.g. the cuboid shape as shown in FIG. 1, which renders mounting of the liquid crystal module 20 and use of the device 10 more convenient. The device 10 can further include a vibrating platform 40 for applying vertical vibration, and the vibrating platform 40 is connected with flanges at the lower ends of the side walls 13 of the cover 11 through fixing members 41, as shown in FIG. 1. The vibrating platform 40 can apply vibration with constant amplitude, so as to ensure the accuracy of detection.

The elastic members 15 can be springs. The springs are selected to ensure that the collision units 14 can effectively collide with the panel 21 of the liquid crystal module 20 but do not damage the panel 21. To reach better collision strength by the collision units 14, the collision units 14 can be metal balls, such as, but not limited to, steel balls. If glass of the panel 21 is relatively thin, relatively light collision units 14 can be selected. If fragments occur during detection, the weight of the collision units 14 should be reduced; in this manner, vibration acceleration can be increased, so as to ensure the detection rate. The surfaces of the collision units 14, which can contact the panel 21 of the liquid crystal module 20, should be spherical surfaces. In an embodiment, the collision units 14 can be balls. In this case, the collision units 14 do not have sharp shapes, so as not to damage, such as scratch the panel 21 when colliding with the panel 21 of the liquid crystal module 20. When the collision units 14 are balls, the distance between each collision unit 14 and the panel 21 of the liquid crystal module 20 is 2 to 3 times the diameter of the spherical collision unit 14.

Because the collision units 14 are connected to the top wall 12 of the cover 11 through the elastic members 15, the collision units 14 can merely collide with the predetermined positions of the panel 21, and the detector can conveniently detect the positions where the panel 21 has maximum abnormity probability based on statistical data, thus improving the detection efficiency. To realize a more comprehensive detection, the elastic members 15 can be connected to the top wall 12 of the cover in a movable mode, so as to facilitate use of the device 10.

A method for detection by using the device 10 will be described below in conjunction with FIGS. 1 and 2.

A cover 11 mounted on a vibrating platform 40 capable of vibrating vertically is provided, and multiple collision units 14 connected to the top wall 12 of the cover 11 through elastic members 15 respectively are arranged in the cover 11. A liquid crystal module 20 to be detected is fixedly connected to the side walls 13 of the cover 11 through connectors 22, and a panel 21 of the liquid crystal module 20 faces the collision units 14.

Figure 2:
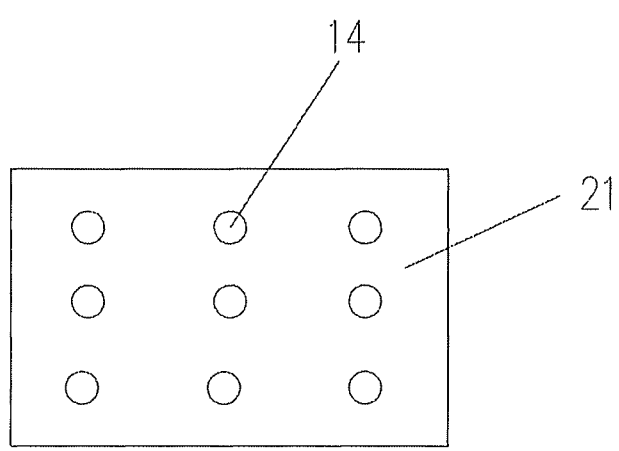
FIG. 2 shows the distribution of collision units according to an embodiment.

Taking a 32-inch liquid crystal module 20 of which panel 21 has a glass thickness of 0.7 mm as an example, nine collision units 14 can be arranged in a Sudoku pattern, as shown in FIG. 2. The elastic members 15 can be springs having an elastic coefficient k of 98 N/m. The collision units 14 are balls with mass of 50 g and diameter of 4 cm, and the distance between the lower end of each spherical collision unit 14 and the panel 21 is 10 cm. The vibrating platform 40 is actuated to vibrate for 30 minutes, with the vibrating parameters being kept as 1 Grm and 1-200 Hz, so as to collide with the panel 21 of the liquid crystal module 20. Later, vibration is stopped, and the liquid crystal module 20 is analyzed.

If necessary, the positions of the elastic members 15 (namely springs) can be changed. Subsequently, the cover 11 is vertically vibrated again to perform collision detection on other positions of the panel 21 of the liquid crystal module 20.

Although the present disclosure has been described with reference to the preferred embodiments, various modifications could be made to the present disclosure without departing from the scope of the present disclosure, and components in the present disclosure could be substituted by equivalents. Particularly, as long as structural conflicts do not exist, all technical features mentioned in all the embodiments may be combined together in any manner. The present disclosure is not limited to the specific embodiments disclosed in the description, but includes all technical solutions falling into the scope of the claims.

The invention claimed is:

1. A device for detecting a quantity of liquid crystal of a liquid crystal module, including a horizontally-arranged covered for fixedly accommodating the liquid crystal module, wherein an accommodation space for accommodating collision units is formed between the liquid crystal module and the cover, the collision units being connected to the top wall of the cover through elastic members, and wherein the collision units are spaced from the liquid crystal module at a certain distance in a static status, and collide with any predetermined/required position of a panel of the liquid crystal module through vibration of the cover in the vertical direction during detection, and wherein the elastic members are connected to the top wall of the cover in such a manner that the position of each elastic member can be changed, wherein in the static status, the distance between the collision unit and the panel of the liquid crystal module is 2 to 3 times the height of the collision unit.

2. The device according to claim 1, wherein the elastic member is a spring.

3. The device according to claim 1, wherein the surface of each collision unit that can contact the panel of the liquid crystal module is configured as spherical surface.

4. The device according to claim 3, wherein each collision unit is designed as a ball.

5. The device according to claim 4, wherein the cover includes side walls extending downwards from the top wall, and a connector for fixing the liquid crystal module is arranged on each side wall.

6. The device according to claim 5, wherein the device further includes a vibrating platform for applying vertical vibration, and the lower end of each side wall is connected with the vibrating platform through a fixing member.

7. A method for detecting the quantity of liquid crystal with the device according to claim 1, including the following steps:
   (a) providing a cover, and arranging a plurality of collision units connected with the top wall of the cover through elastic members respectively in the cover;
   (b) fixedly accommodating a liquid crystal module to be detected in the cover in such a manner that the liquid crystal module is spaced from the collision units in a certain distance, a panel of the liquid crystal module facing the collision units;
   (c) vertically vibrating the cover so that the collision units collide with the panel of the liquid crystal module; and
   (d) stopping vibration of the cover, and taking the liquid crystal module out for analyzing.

8. The method according to claim 7, wherein after step (d), the elastic members are moved, and then the cover is vertically vibrated again to collide with other positions of the panel of the liquid crystal module.

* * * * *